(12) United States Patent
Ji

(10) Patent No.: US 11,166,682 B2
(45) Date of Patent: Nov. 9, 2021

(54) SYSTEMS AND METHODS FOR MEDICAL IMAGING

(71) Applicant: SHANGHAI UNITED IMAGING HEALTHCARE CO., LTD., Shanghai (CN)

(72) Inventor: Zijun Ji, Shanghai (CN)

(73) Assignee: SHANGHAJ UNITED IMAGING HEALTHCARE CO., LTD., Shanghai (CN)

( * ) Notice: Subject to any disclaimer, the term of this patent is extended or adjusted under 35 U.S.C. 154(b) by 526 days.

(21) Appl. No.: 15/981,277

(22) Filed: May 16, 2018

(65) Prior Publication Data

US 2018/0333111 A1 Nov. 22, 2018

(30) Foreign Application Priority Data

May 16, 2017 (CN) .......................... 201710342956.3

(51) Int. Cl.
*A61B 6/04* (2006.01)
*A61B 6/00* (2006.01)
(Continued)

(52) U.S. Cl.
CPC .............. *A61B 6/0492* (2013.01); *A61B 6/46* (2013.01); *G01R 33/283* (2013.01);
(Continued)

(58) Field of Classification Search
CPC ........... A61B 6/04; A61B 6/46; A61B 6/0492; A61B 6/032; A61B 6/037; A61B 5/055;
(Continued)

(56) References Cited

U.S. PATENT DOCUMENTS 6,226,031 B1 * 5/2001 Barraclough ........... G06T 9/007
348/14.01
6,564,080 B1 * 5/2003 Kimura ................ A61B 5/0263
324/307
(Continued)

FOREIGN PATENT DOCUMENTS

CN 202268173 U 6/2012
CN 202654140 U 1/2013
(Continued)

OTHER PUBLICATIONS

Siemens [CN 106385632 A, translation as provided in IDS of May 16, 2018], (Year: 2017).*
(Continued)

*Primary Examiner* — Oommen Jacob
(74) *Attorney, Agent, or Firm* — Metis IP LLC

(57) ABSTRACT

A system for medical imaging is provided. The system includes a scanning device configured with a scanning cavity, a control device, and an output device configured within the scanning cavity. The control device is configured to obtain one or more scan protocols and acquire at least one guide instruction corresponding to the one or more scan protocols. The output device is configured to obtain guide information corresponding to the at least one guide instruction and present the guide information. The scanning device is configured to scan a subject with the presentation of the guide information according to the one or more scan protocols.

20 Claims, 12 Drawing Sheets

(51) Int. Cl.
  *G01R 33/54* (2006.01)
  *G01R 33/28* (2006.01)
  *A61N 5/10* (2006.01)
  *A61B 6/03* (2006.01)
  *G01R 33/20* (2006.01)

(52) U.S. Cl.
  CPC ............ *G01R 33/543* (2013.01); *A61B 6/032* (2013.01); *A61B 6/037* (2013.01); *A61N 5/10* (2013.01); *A61N 2005/1092* (2013.01); *G01R 33/20* (2013.01); *G06T 2211/40* (2013.01)

(58) Field of Classification Search
  CPC .. A61B 5/0037; A61B 5/0555; G01R 33/543; G01R 33/283; G01R 33/20; G01R 33/307; G01R 33/282; G01R 33/3806; G01R 33/281; A61N 5/10; A61N 2005/1092; G06T 2211/40; H04N 9/80; H04N 21/440281; H04N 5/783; H04N 9/8205; H04N 21/4334; H04N 5/775; H04N 9/87; H04N 21/4147; G11B 27/322; G11B 27/005
  See application file for complete search history.

(56) References Cited

U.S. PATENT DOCUMENTS

| | | | | |
|---|---|---|---|---|
| 6,961,604 | B1* | 11/2005 | Vahasalo | G01R 33/283 324/318 |
| 7,212,727 | B2* | 5/2007 | Senoh | G11B 27/005 386/351 |
| 8,712,798 | B2* | 4/2014 | Gotman | A61B 6/00 705/3 |
| 9,597,051 | B2* | 3/2017 | Gatayama | A61B 6/54 |
| 2003/0215209 | A1* | 11/2003 | Kawaguchi | G11B 27/005 386/329 |
| 2005/0114140 | A1* | 5/2005 | Brackett | G10L 15/01 704/270 |
| 2006/0036948 | A1* | 2/2006 | Matsuzaka | G11B 27/28 715/723 |
| 2006/0074305 | A1* | 4/2006 | Mostafavi | A61B 6/032 600/428 |
| 2006/0079763 | A1* | 4/2006 | Jeung | A61B 6/032 600/428 |
| 2006/0173270 | A1* | 8/2006 | Weiner | A61B 6/467 600/407 |
| 2006/0241455 | A1* | 10/2006 | Shvarts | A61B 8/08 600/447 |
| 2007/0109294 | A1* | 5/2007 | Gotman | A61B 6/467 345/418 |
| 2008/0064951 | A1* | 3/2008 | Kitane | G01R 33/5676 600/413 |
| 2009/0048505 | A1* | 2/2009 | Kuth | G01R 33/282 600/410 |
| 2011/0210734 | A1* | 9/2011 | Darrow | G06K 9/6284 324/309 |
| 2011/0301461 | A1* | 12/2011 | Anite | A61B 8/467 600/443 |
| 2011/0313232 | A1* | 12/2011 | Balakin | H05H 13/04 600/1 |
| 2012/0002780 | A1* | 1/2012 | Forthmann | A61B 6/037 378/4 |
| 2012/0134646 | A1* | 5/2012 | Alexander | G11B 27/322 386/241 |
| 2013/0011116 | A1* | 1/2013 | Barrett | G11B 27/28 386/230 |
| 2018/0333111 | A1* | 11/2018 | Ji | G01R 33/543 |

FOREIGN PATENT DOCUMENTS

| | | | |
|---|---|---|---|
| CN | 103654821 | A | 3/2014 |
| CN | 104188680 | A | 12/2014 |
| CN | 104810016 | A | 7/2015 |
| CN | 106365632 | A | 2/2017 |
| CN | 106385632 | A * | 2/2017 |

OTHER PUBLICATIONS

First Office Action in Chinese Application No. 201710342966.3 dated Nov. 5, 2019, 16 pages.
Li, Maoqing et al., Basic Knowledge of Computer, National Computer Rank Examination Level 1 Course, 2003, 7 pages.

* cited by examiner

SYSTEMS AND METHODS FOR MEDICAL IMAGING

CROSS REFERENCE

The present application claims priority of Chinese Patent Application No. 201710342956.3 filed on May 16, 2017, the content of which is hereby incorporated by reference in its entirety.

TECHNICAL FIELD

The present disclosure generally relates to a medical device, and more particularly, to systems and methods for acquiring medical imaging data.

BACKGROUND

During a medical imaging procedure, a patient is often guided to conduct one or more specific actions to acquire medical imaging data. In general, the patient is guided by an operator of a medical imaging device via voice instructions. The voice instructions may be verbally generated in real-time by the operator. Alternatively, the voice instructions may be pre-recorded and played by the operator according to the medical imaging procedure. However, current guiding techniques rely on the operator of the medical imaging device, which is time-consuming and inefficient. Therefore, it is desirable to develop methods and systems to efficiently guide the patient during the medical imaging procedure.

SUMMARY

According to an aspect of the present disclosure, a system is provided. The system may include a scanning device configured with a scanning cavity, a control device, and an output device configured within the scanning cavity. The control device may be configured to obtain one or more scan protocols and acquire at least one guide instruction corresponding to the one or more scan protocols. The output device may be configured to obtain guide information corresponding to the at least one guide instruction and present the guide information. The scanning device may be configured to scan a subject with the presentation of the guide information according to the one or more scan protocols.

In some embodiments, the system may further include a decoding device configured to decode the guide information and send the decoded guide information to the output device.

In some embodiments, the decoding device may further be configured to extract the guide information from the at least one guide instruction.

In some embodiments, the decoding device may further be configured to acquire a storage location of the guide information and retrieve the guide information from the storage location.

In some embodiments, the at least one guide instruction may include device information and play information. The decoding device may further be configured to send the decoded guide information to the output device according to the device information and the play information.

In some embodiments, the at least one guide instruction may include device information and play information. The decoding device may further be configured to send the decoded guide information and the play information to the output device according to the device information. The output device may further be configured to present the decoded guide information according to the play information.

In some embodiments, the play information may include at least one of a play mode, a play interval, a starting point, or a pre-set number of playbacks.

In some embodiments, the guide information may include at least one of a picture, an audio, or a video.

In some embodiments, the presentation of the guide information may be synchronous to the scanning of the subject according to the one or more scan protocols.

In some embodiments, the output device may include at least one of a display, a projector, or a head-mounted virtual reality device.

According to an aspect of the present disclosure, a method is provided. The method may be implemented on a system, including at least one processor and a storage device. The method may include obtaining one or more scan protocols; acquiring at least one guide instruction corresponding to the one or more scan protocols; obtaining guide information corresponding to the at least one guide instruction; presenting the guide information via an output device; and scanning a subject with the presentation of the guide information according to the one or more scan protocols.

According to an aspect of the present disclosure, a non-transitory computer readable medium is provided. The non-transitory computer readable medium may include instructions configured to cause a computing system to obtain one or more scan protocols; acquire at least one guide instruction corresponding to the one or more scan protocols; obtain guide information corresponding to the at least one guide instruction; present the guide information via an output device; and scan a subject with the presentation of the guide information according to the one or more scan protocols.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1A:
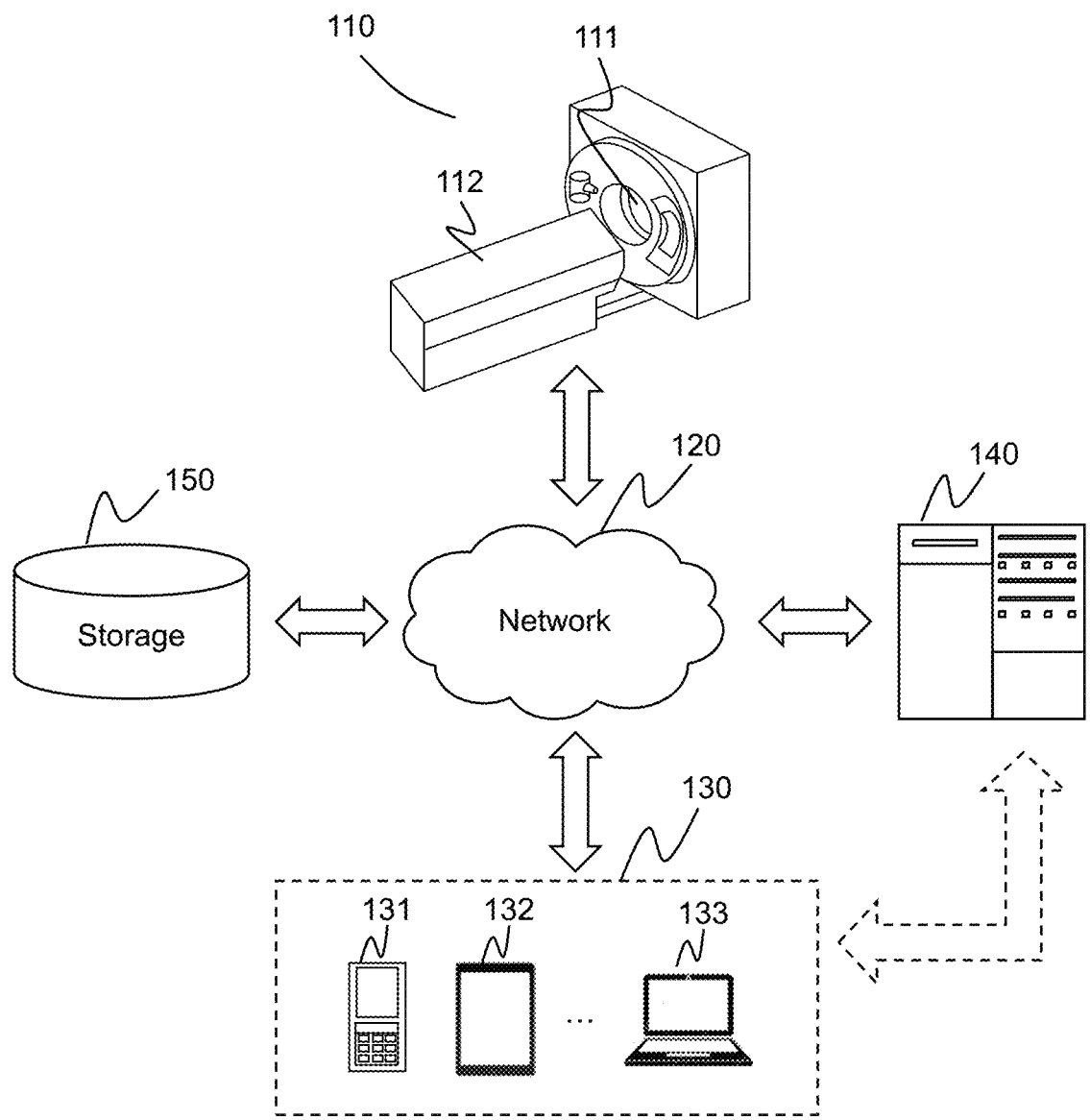
FIGS. 1A and 1B are schematic diagrams illustrating an exemplary system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "module," "unit," and/or "block" used herein are one method to distinguish different components, elements, parts, section or assembly of different level in ascending order. However, the terms may be displaced by other expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., CPU 220 illustrated in FIG. 2) may be provided on a computer-readable medium, such as a compact disc, a digital video disc, a flash drive, a magnetic disc, or any other tangible medium, or as a digital download (and can be initially stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a engine, module, unit or block is referred to as being "on," "connected to," or "coupled to," another engine, module, unit or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Moreover, the system and method in the present disclosure is described primarily in regard to guiding a patient to conduct one or more specific actions in the scanning of a medical device. In some embodiments, the system and the method may obtain one or more scan protocols, and acquire at least one guide instruction corresponding to the one or more scan protocols. In some embodiments, the system and the method may further obtain guide information corresponding to the at least one guide instruction, and present the guide information. In some embodiments, the system and the method may further scan a subject with the presentation of the guide information.

Figure 1B:
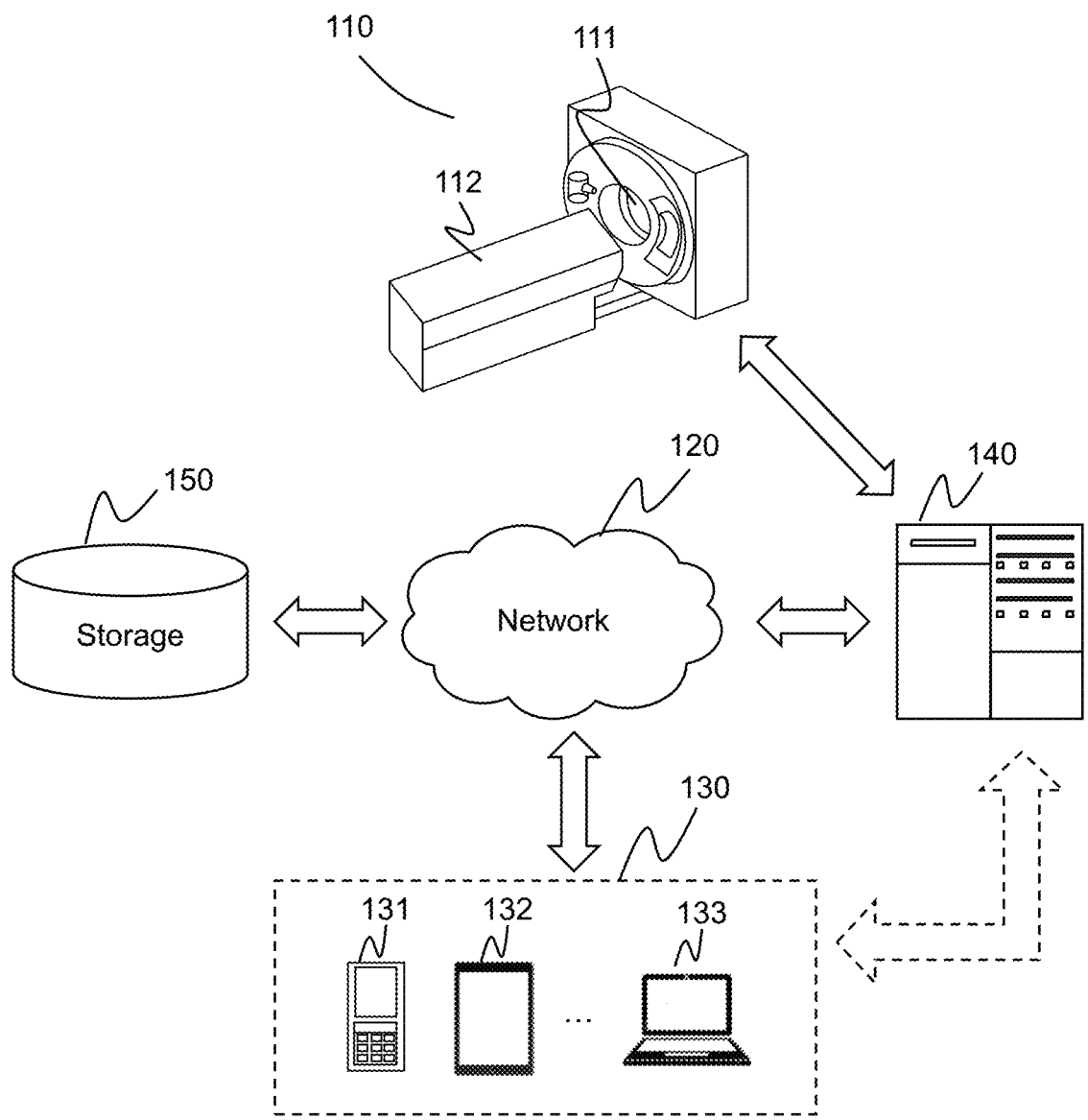

FIGS. 1A and 1B are schematic diagrams illustrating an exemplary medical system 100 according to some embodiments of the present disclosure. According to the embodiment shown in FIG. 1A, the medical system 100 may include a medical device 110, a network 120, one or more terminals 130, a processing device 140, and a storage 150.

The medical device 110 may scan a subject (e.g., a patient) and generate medical imaging data. The medical device 110 may include a scanning cavity (also referred as imaging area) 111, a table 112, etc. The scanning cavity 111 may be configured to define an imaging area. The subject lying on the table 112 may be configured within the scanning cavity to be scanned. In some embodiments, the medical device may include a computed tomography (CT), a cone beam computed tomography (CBCT), an emission computed tomography (ECT), a magnetic resonance imaging (MRI), a radiotherapy (RT) device, a positron emission computed tomography (PET), or the like, or any combination thereof. In some embodiments, the medical device 110 may present guide information during a scanning of the medical device 110. The guide information may be configured to guide the subject to conduct one or more specific actions. In some embodiments, the medical device 110 may include a scanning device, a control device, a decoding device, and an output device. Details regarding to the medical device 110 may be found in connection with FIG. 4 and the descriptions thereof.

The network 120 may include any suitable network that can facilitate exchange of information and/or data for the medical system 100. In some embodiments, one or more components of the medical system 100 (e.g., the medical device 110, the terminal 130, the processing device 140, the storage 150) may communicate with one or more other components of the medical system 100 via the network 120. For example, the medical device 110 may obtain guide information from the storage 150 via the network 120. As another example, the medical device 110 may obtain one or more scan protocols from the storage 150 and/or the processing device 140. As still another example, the processing device 140 may obtain medical imaging data from the medical device 110 via the network 120. The network 120 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the medical system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™ a Gear VR™. In some embodiments, the terminal(s) 130 may be part of the processing device 140.

The processing device 140 may process medical imaging data generated by the medical device 110. In some embodiments, the processing device 140 may generate one or more guide instructions according to one or more scan protocols. The processing device 140 may obtain guide information corresponding to the one or more guide instructions. The processing device 140 may present the guide information during a scanning of the medical device 110. In some embodiments, the processing device 140 may cause the medical device 110 to conduct one or more operations described as above. For example, the processing device 140 may cause the medical device 110 to obtain one or more scan protocols and generate one or more guide instructions according to the one or more scan protocols. As another example, the processing device 140 may cause the medical device 110 to obtain and present guide information during a scanning of the medical device 110. Further, the processing device 140 may cause the medical device 220 to scan a subject with the presentation of the guide information.

Figure 2:
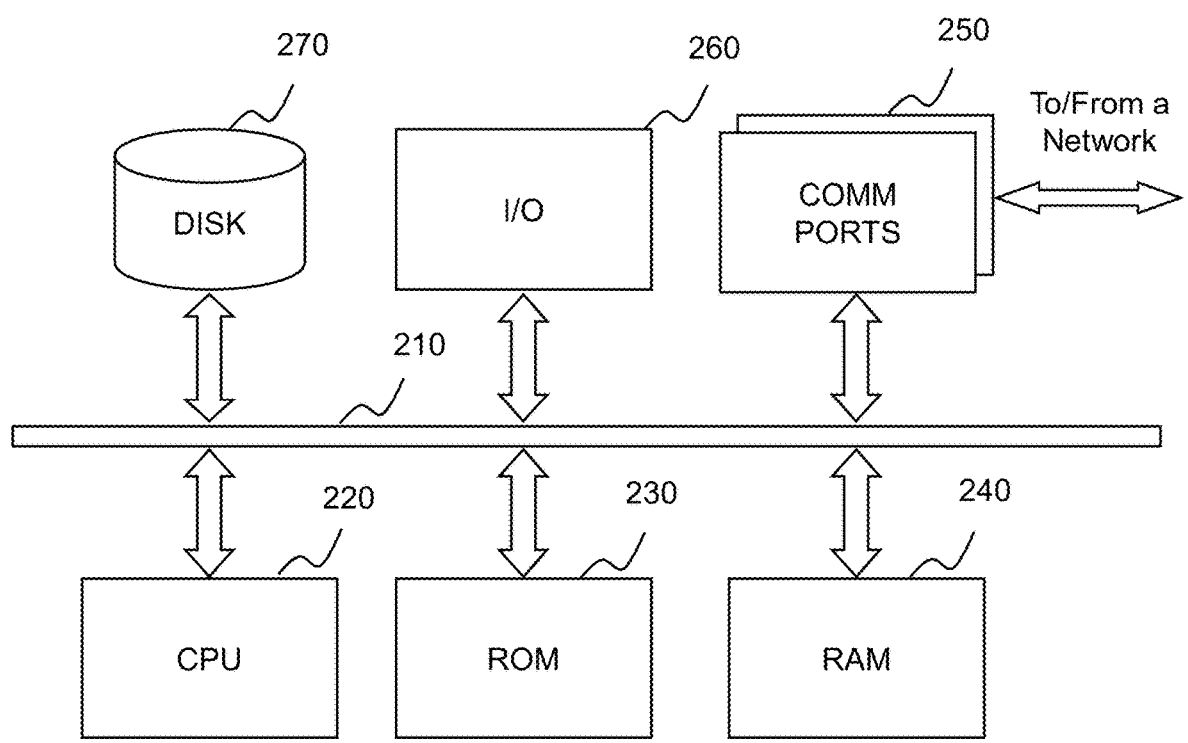
FIG. 2 is a schematic diagram illustrating an exemplary computing device on which the system can be implemented, according to some embodiments of the present disclosure.

In some embodiments, the processing device 140 may be a single server or a server group. The server group may be centralized or distributed. In some embodiments, the processing device 140 may be local or remote from other components in the medical system 100. Alternatively, the processing device 140 may be directly connected to the medical device 110, the terminal 130 and/or the storage 150. In some embodiments, the processing device 140 may be implemented on a cloud platform to perform processing. For example, the processing device 140 may be implemented on the cloud platform to detect whether a collision between a component of the medical device 110 and a subject, adjust the geometry of the medical device 110, perform trajectory planning, or the like, or a combination thereof. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage 150 may store information, data, instructions, and/or any other information. In some embodiments, the storage 150 may store a plurality of scan protocols. In some embodiments, the storage 150 may store guide information, play information (described below), information relating to an output device. The guide information, the play information, and the information relating to an output device may be used to generate one or more guide instructions. Further, the storage 150 may store the one or more guide instructions. In some embodiments, the storage 150 may store medical imaging data obtained from the medical imaging device 110. In some embodiments, the storage 150 may store data and/or instructions that the processing device 140 may execute or use to perform exemplary methods described in the present disclosure. In some embodiments, the storage 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage 150 may be connected to the network 120 to communicate with one or more other components in the medical system 100 (e.g., the medical device 110, the processing device 140, the terminal 130). One or more components of the medical system 100 may access the information or instructions stored in the storage 150 via the network 120. In some embodiments, the storage 150 may be directly connected to or communicate with one or more other components of the medical system 100 (e.g., the processing device 140, the terminal 130). In some embodiments, the storage 150 may be part of the processing device 140.

The embodiment shown in FIG. 1B is similar to the embodiment shown in FIG. 1A, except that the medical device 110 and the processing device 140 are connected directly instead of via the network 120.

FIG. 2 is a schematic diagram illustrating an exemplary computing device 200 on which the medical system 100 can be implemented, according to some embodiments of the present disclosure.

The computing device 200 may be a general purpose computer or a special purpose computer. Both may be used to implement a medical system of the present disclosure. The computing device 200 may be used to implement any component of the service as described herein. For example, one or more components of the medical device 110 and the processing device 140 of the medical system 100 may be implemented on the computing device 200, via its hardware, software program, firmware, or a combination thereof. Although only one such computer is shown for convenience, the computer functions related to the medical system 100 as described herein may be implemented in a distributed manner on a number of similar platforms to distribute the processing load.

The computing device 200, for example, may include COMM ports 250 connected to and from a network (e.g., the network 120) connected thereto to facilitate data communications. The computing device 200 may also include a central processing unit (CPU) 220, in the form of one or more processors, for executing program instructions. The exemplary computer platform may include an internal communication bus 210, program storage and data storage of different forms, for example, a disk 270, and a read only memory (ROM) 230, or a random access memory (RAM) 240, for various data files to be processed and/or transmitted by the computer. The exemplary computer platform may also include program instructions stored in the ROM 230, the RAM 240, and/or other type of non-transitory storage medium to be executed by the CPU 220. The methods and/or processes of the present disclosure may be implemented as the program instructions. The computing device 200 also includes an I/O 260, supporting input/output between the computer and other components therein. The computing device 200 may also receive programming and data via network communications.

Merely for illustration, only one CPU and/or processor is described in the computing device 200. However, it should be noted that the computing device 200 in the present disclosure may also include multiple CPUs and/or processors, thus operations and/or method steps that are performed by one CPU and/or processor as described in the present disclosure may also be jointly or separately performed by the multiple CPUs and/or processors. For example, the CPU and/or processor of the computing device 200 executes both step A and step B. As in another example, step A and step B may also be performed by two different CPUs and/or processors jointly or separately in the computing device 200 (e.g., the first processor executes step A, and the second processor executes step B; or the first and second processors jointly execute steps A and B).

Figure 3:
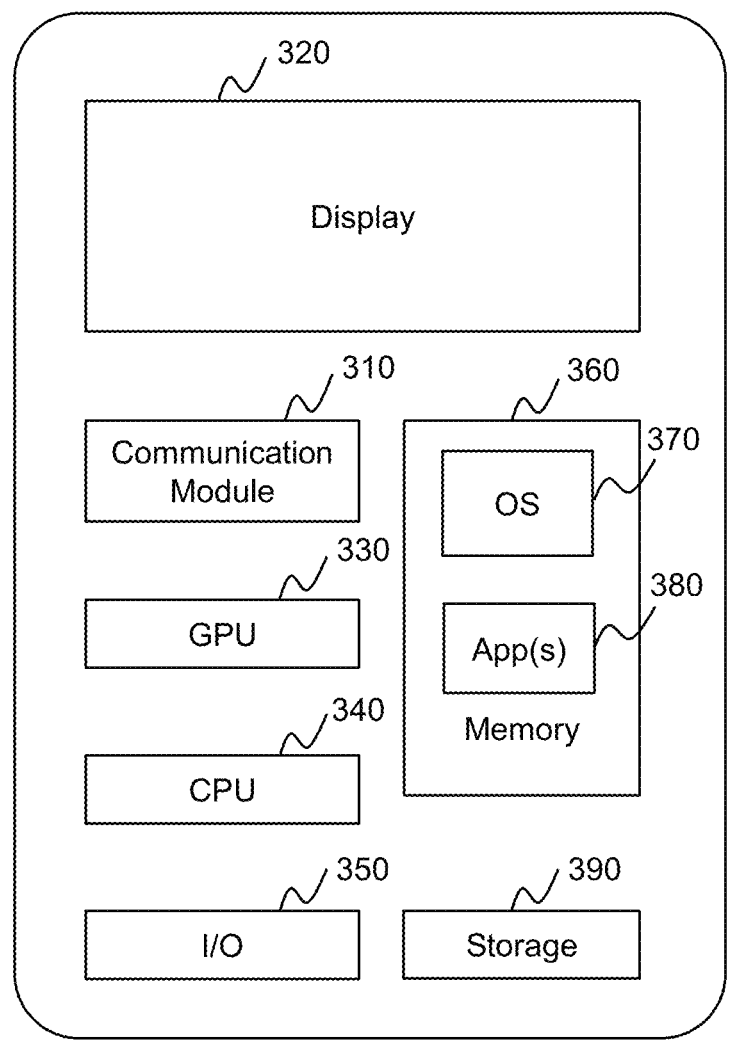
FIG. 3 is a schematic diagram illustrating exemplary hardware and/or software components of an exemplary mobile device on which the terminal may be implemented according to some embodiments of the present disclosure.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication module 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the medical system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
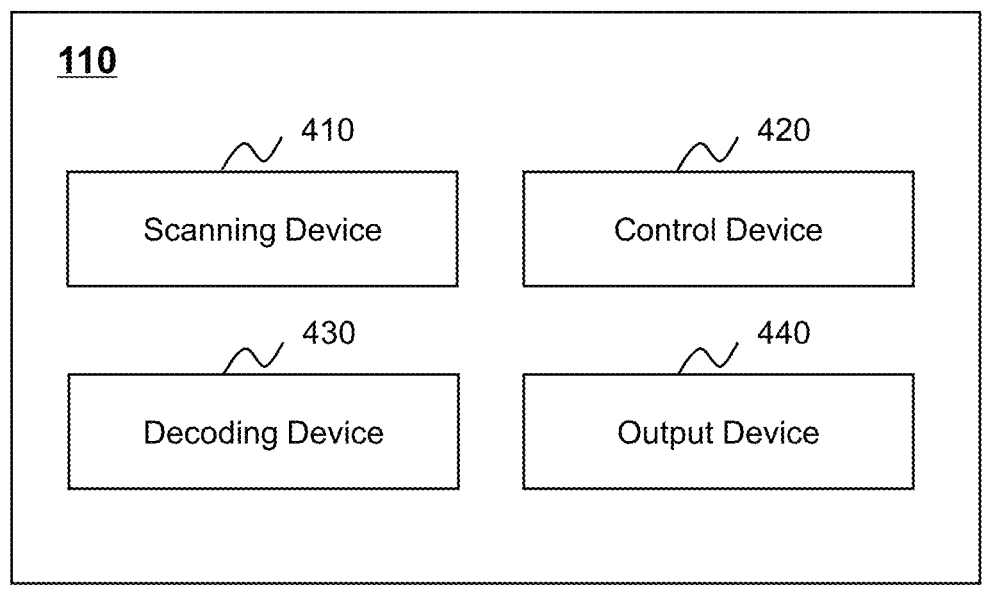
FIG. 4 is a block diagram illustrating an exemplary medical device according to some embodiments of the present disclosure.

FIG. 4 is a block diagram illustrating an exemplary medical device 110 according to some embodiments of the present disclosure. The medical device 110 may include a scanning device 410, a control device 420, a decoding device 430, and an output device 440. One or more components of the medical device 110 may be implemented on various components (e.g., the CPU 220 of the computing device 200 illustrated in FIG. 2). More or less components may be included in the medical device 110 without loss of generality. For example, two of the devices may be combined into a single device, or one of the devices may be divided into two or more devices.

The scanning device 410 may scan a subject and generate medical imaging data. In some embodiments, the scanning device 410 may include a scanning cavity (e.g., the scanning cavity 111). The subject may be configured within the scanning cavity to be scanned. In some embodiments, the scanning device 410 may scan the subject according to one or more scanning protocols. As used in the present disclosure, a scanning protocol may include information relating to a patient (e.g., a name, a gender, an age), a medical record of the patient, a scanning type (e.g., CT scanning, MRI scanning, more particularly, CT scanning of head, MRI scanning of chest) and one or more scanning parameters. Further, the scanning protocol may also include information of the scanning device 410, information of the output device 440, information relating to guide information (described below), or any other information (e.g., play information described below). As used herein, the scanning device 410 may correspond to the scanning type. The output device 440 may correspond to the scanning device 410. The information of a device (e.g., the scanning device 410, the output device 440) may refer to information that can identify the device, for example, an identifier, a name, a serial number. For the purposes of brevity, in the present disclosure, device information may refer to the information of the output device 410.

The control device 420 may acquire one or more scanning protocols and obtain at least one guide instruction based on the one or more scanning protocols. The at least one guide instruction may include information relating to guide information, device information, play information, etc. The information relating to guide information may include the guide information itself (e.g., original guide information, encoded guide information), and/or a storage location of the guide information (e.g., stored in the storage 150). The guide information may be configured to guide a subject to conduct a specific action so as to satisfy a requirement of the one or more scanning protocols. The guide information may take the form of a picture, an audio, a video, or the like, or a combination thereof. The play information may be configured to control the presentation and/or decoding of the guide information. The play information may include a play mode, a play interval, a starting point to play the guide information, the pre-set number of playbacks, or the like, or a combination thereof. In some embodiments, the control device 420 may generate the at least one guide instruction. For example, the control device 420 may extract the guide information, the play information, and the device information from the one or more scanning protocols. Then, the control device 420 may generate the at least one guide instruction based on the extracted information. As another example, the control device 420 may generate the at least one guide instruction according to a plurality of relationships, which may be found in connection with FIG. 5 and the descriptions thereof.

Further, the control device 420 may communicate information with other device (e.g., the scanning device 410, the output device 440, the decoding device 430). For example, the control device 420 may send the one or more scan protocols to the scanning device 410. As another example, the control device 420 may send the at least one guide information to the output device 440 and/or the decoding device 430.

The decoding device 430 may obtain and decode guide information according to at least one guide instruction. In some embodiments, the decoding device 430 may obtain the guide information by performing one or more operations as described in connection with the output device 440. For example, the decoding device 430 may extract the guide information from the at least one guide instruction. As another example, the decoding device 430 may acquire a storage location of the guide information, and retrieve the guide information from the storage location. In some embodiments, the decoding device 430 may decode the guide information (herein, referred as encoded guide information) according to the play information. Accordingly, the decoded guide information may satisfy a requirement defined by the play information and can be presented directly by the output device 440. That is, the output device 440 may present the decoded guide information immediately with no further need to refer to the play information. In some other embodiments, the decoding device 430 may decode the guide information directly without referring to the play information. Further, the decoding device 430 may send the guide information to the output device 440 Thus, the output device 440 may present the decoded guide information according to the play information. In some embodiments, the decoding device 430 may send the guide information via the network 120.

The output device 440 may obtain and present guide information according to at least one guide instruction. In some embodiments, the output device 440 may obtain the guide information based on the at least one guide instruction. For example, the output device 440 may extract the guide information from the at least one guide instruction. As another example, the output device 440 may acquire a storage location of the guide information, and retrieve the guide information from the storage location. In some embodiments, the output device 440 may present the guide information according to the play information. For example, if the starting point of the play information is the same as the beginning of the scanning of the scanning device 410, the output device 440 may present the guide information when the scanning device 410 starts to scan. Further, for the guide information decoded according to the play information, the output device 440 may present the guide information without referring to the play information.

In some embodiments, the output device 440 may include a display, a projector, a virtual reality (VR) device (e.g., a head-mounted VR device), a loudspeaker box, or the like, or a combination thereof. The display may include a light emitting diode (LED), a liquid crystal display (LCD), etc. In some embodiments, the output device 440 may include one or more devices described in connection with the terminal 130. For example, the output device 130 may include a wearable device, for example, a bracelet, a footgear, eyeglasses, a helmet, a watch, clothing, a backpack, a smart accessory.

Figure 7:
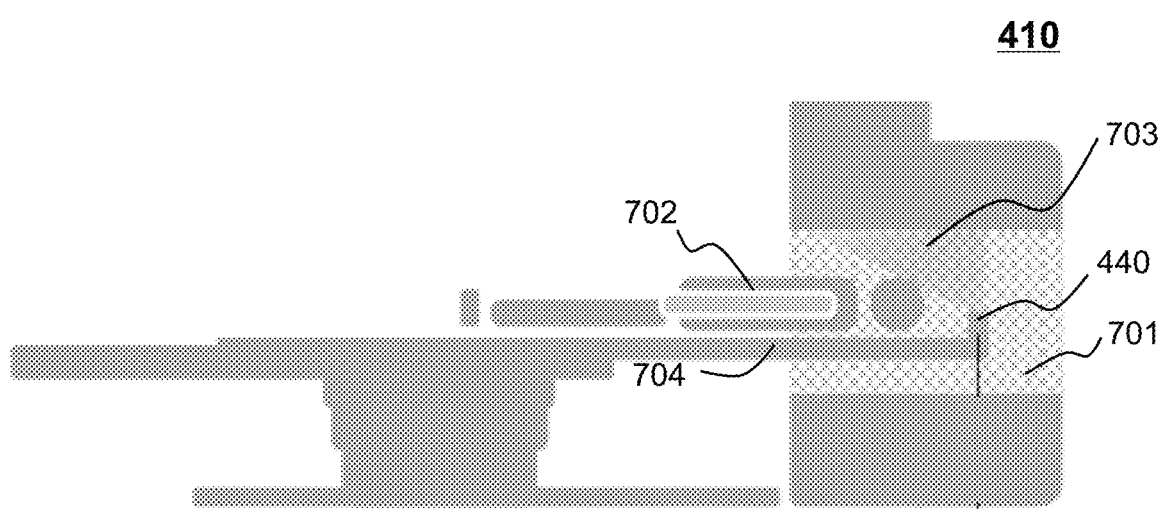
FIG. 7 illustrates an exemplary position relationship between an output device and a scanning device according to some embodiments of the present disclosure.

In some embodiments, the output device 440 may be configured on the scanning device 410, e.g., within the scanning cavity of the scanning device 410. FIG. 7 illustrates an exemplary position relationship between the output device 440 (herein referred as a projector) and the scanning device 410 according to some embodiments of the present disclosure. As illustrated, the scanning device 410 may include a scanning cavity 701 and a table 704. A patient 702 may lie on the table 704, and part of the table 704 may be configured within the scanning cavity 701. The output device 440 may be configured within the scanning cavity 701 without influencing the scanning of the patient 702. For example, the output device 440 may be configured in the backend of the scanning cavity 701. The table 704 may be moved to transfer the patient 702 to the scanning cavity 701 to be adjacent to the output device 440. The output device 440 may further include a projection screen on a top ceiling of the scanning cavity 701 to present the guide information to the patient during scan. Accordingly, the output device 440 may guide the patient 702 directly without influencing the scanning of the patient 702.

It should be noted that the description above is merely an example and is not intended to be limiting. In some embodiments, the output device 440 may not be configured on the scanning device 410. For example, as a VR device or a wearable device, the output device 440 may be worn by the patient 702. As another example, as a loudspeaker box, the output device 440 may be configured anywhere, as long as the patient 702 can hear the voice outputted by the output device 440.

In some embodiments, one or more devices illustrated in FIG. 4 may be implemented in at least part of the exemplary system as illustrated in FIGS. 1A and 1B. For example, the output device 440 and the decoding device 430 may be integrated into a device (not shown). The device may be configured to decode guide information and present the guide information according to at least one guide instruction. As another example, the medical device 110 may further include a storage device configured to store information, for example, medical imaging data, guide information, play information.

Figure 5:
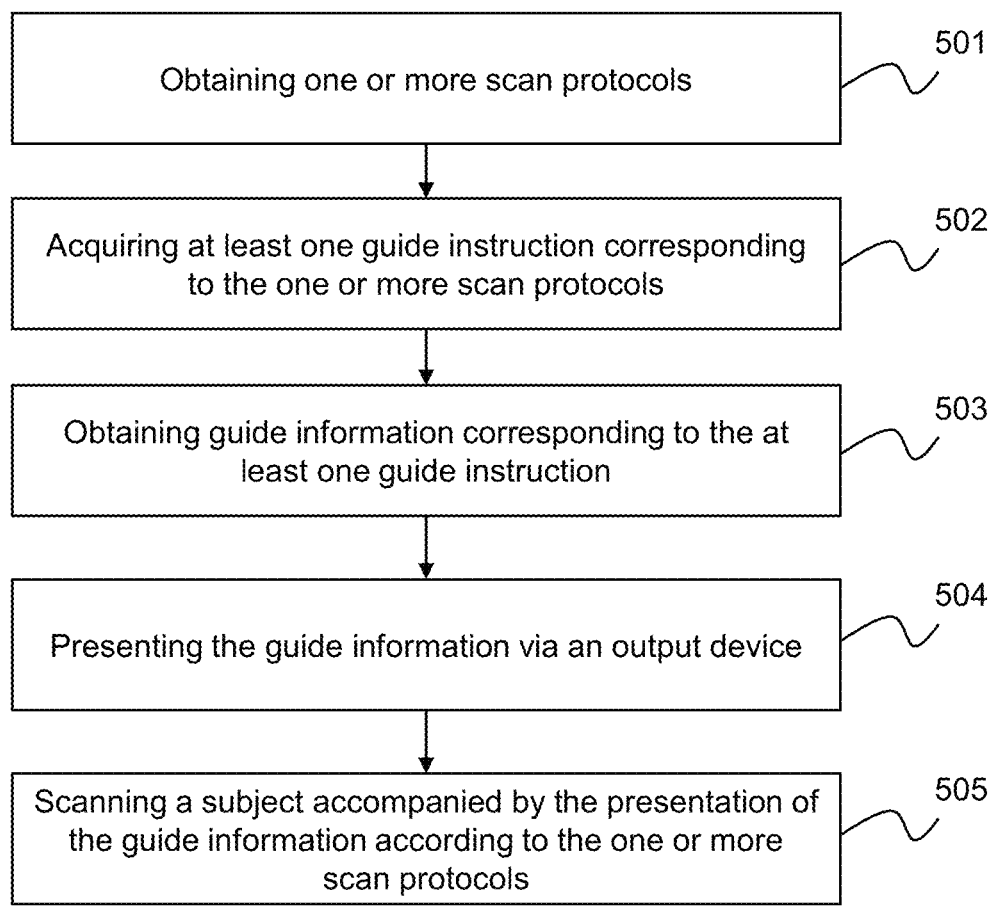
FIG. 5 is a flowchart illustrating an exemplary process for scanning a subject according to some embodiments of the present disclosure.

FIG. 5 is a flowchart illustrating an exemplary process for scanning a subject according to some embodiments of the present disclosure. Process 500 may be performed by processing logic that comprises hardware (e.g., circuitry, dedicated logic, programmable logic, microcode, etc.), software (e.g., instructions run on a processing device to perform hardware simulation), or a combination thereof. In some embodiments, process 500 may be performed by or be implemented on the medical device 110 and/or the processing device 140 of the medical system 100. The CPU 220 of the processing device 140 may execute the set of instructions and may accordingly perform the steps in the flowchart 500.

In 501, the control device 420 may obtain one or more scan protocols. In some embodiments, the one or more scan protocols may be input manually, for example, by an administrator (e.g., a doctor). In some embodiments, the one or more scan protocols may be generated automatically, for example, by the medical device 110 and/or the processing device 140. The one or more scan protocols may correspond to one or more scanning procedures associated with a same patient.

In 502, the control device 420 may acquire at least one guide instruction corresponding to the one or more scan protocols. As illustrated elsewhere in the present disclosure, a guide instruction may include information relating to guide information, play information, device information, etc. The control device 420 may acquire the guide instruction according to the one or more scan protocols. For example, the control device 420 may extract the play information, the device information, and the information relating to guide information from the one or more scan protocols. As another example, the control device 420 may acquire the play information, the device information, and the information relating to guide information according to a plurality of relationships. The plurality of relationships may include a first relationship between the one or more scan protocols and the guide information, a second relationship between the one or more scan protocols and the output devices 440, a third relationship between the one or more scan protocols and the play information, a fourth relationship between the output devices 440 and the guide information, etc. For the first relationship, one or more protocols may correspond to same guide information or a combination of different guide information. Thus, the control device 420 may acquire the guide information according to the first relationship. For example, the control device 420 may acquire a storage location of the guide information according to the first relationship and retrieve the guide information from the storage location. For the second relationship, one or more protocols may correspond to one or more output devices 430. Thus, the control device 420 may determine one or more output devices 430 (i.e., the device information) corresponding to the one or more scan protocols according to the second relationship. More particularly, when the control device 420 determines two or more output devices 440 and a combination of different guide information, the control device 420 may further determine the fourth relationship between each of the two or more output devices 440 and the corresponding guide information of the combination of different guide information. For the third relationship, one or more protocols may correspond to same play information, or a combination of different play information. Thus, the control device 420 may determine the play information according to the third relationship.

In some embodiments, the control device 420 may send the one or more scan protocols to the scanning device 410. In some embodiments, the control device 420 may send the at least one guide instruction to the output device 440. The sending may be conducted via the network 120.

Figure 8:
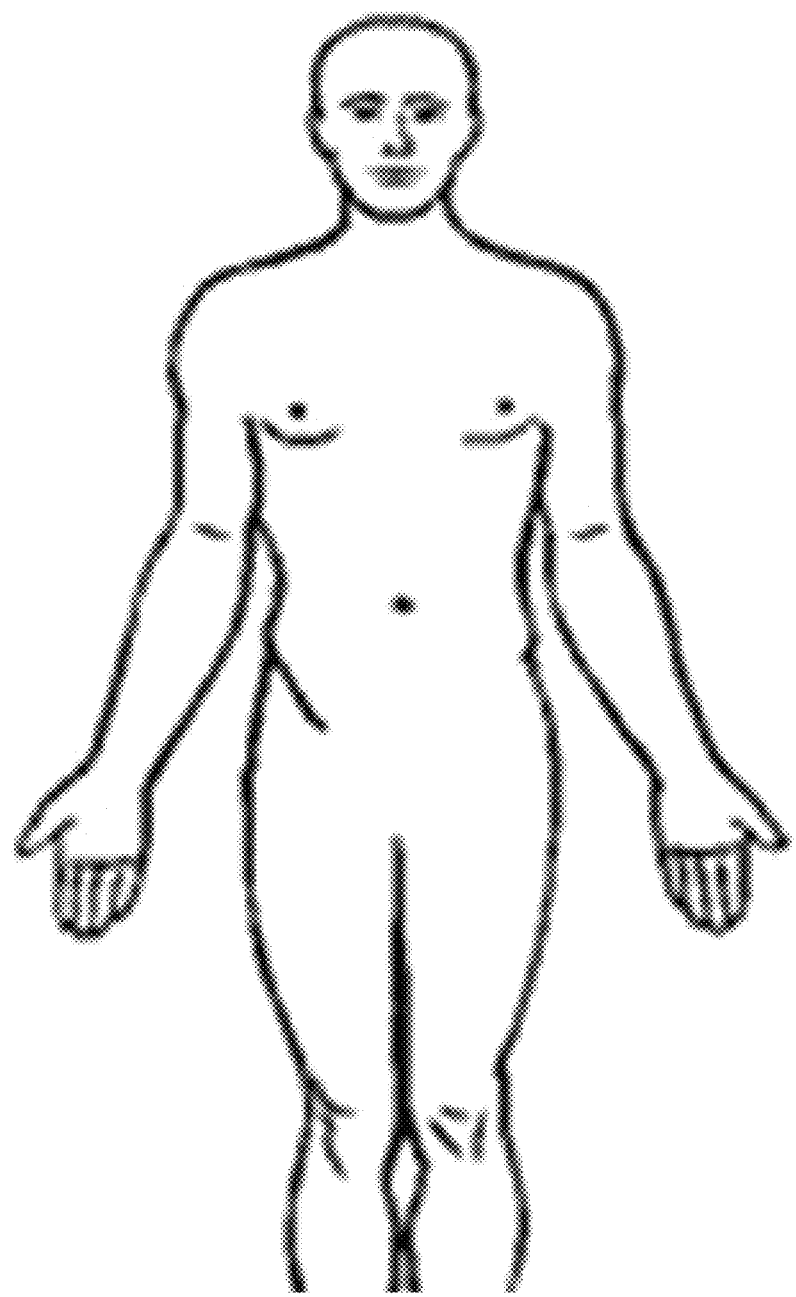
FIGS. 8 through 11 illustrate exemplary guide pictures according to some embodiments of the present disclosure
Figure 9:
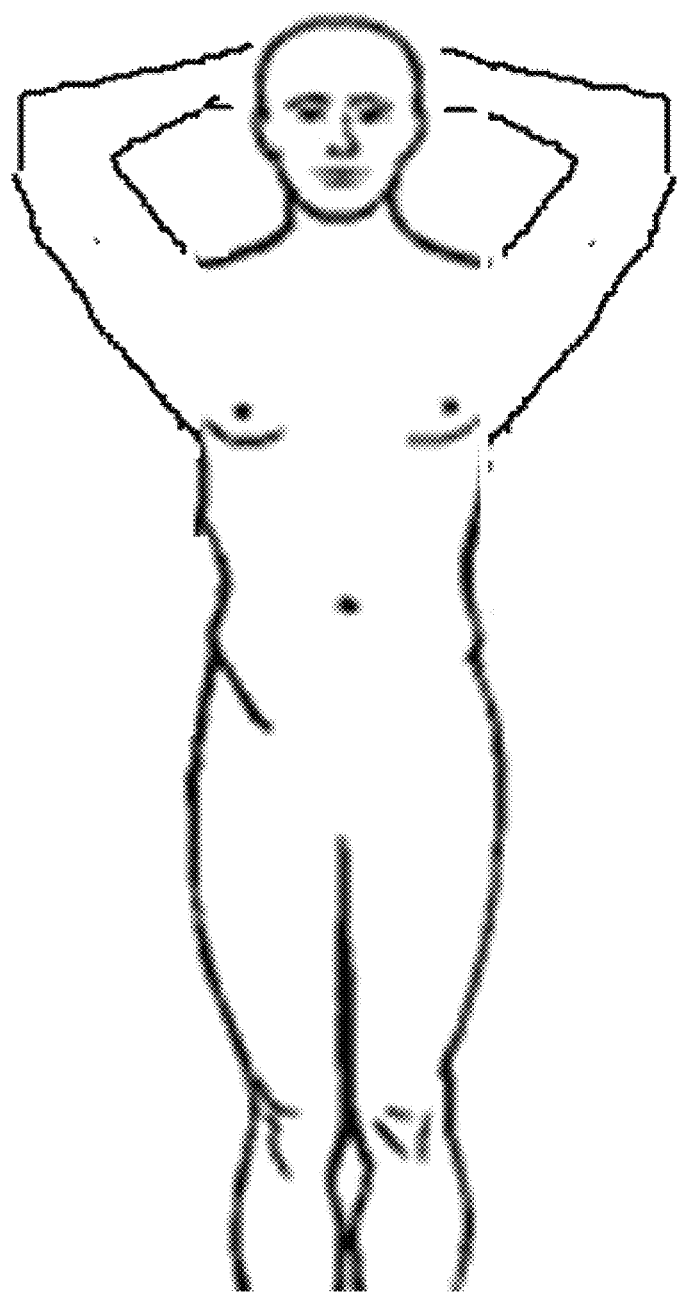
Figure 10:
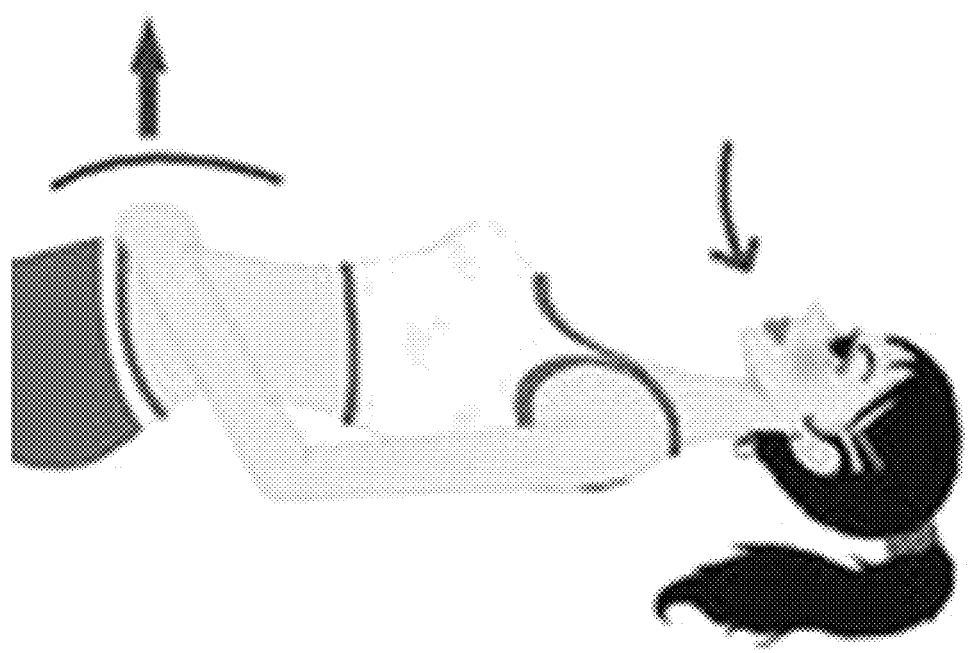
Figure 11:

In 503, the output device 440 may obtain guide information corresponding to the at least one guide instruction. The guide information may include original guide information or encoded guide information. In some embodiments, the output device 440 may extract the guide information from the at least one guide instruction. In some embodiments, the output device 440 may extract a storage location of the guide information. The output device 440 may further retrieve the guide information from the storage location of the guide information. The storage location may include a specific location (e.g., in the storage 150, in the decoding device 430, in the control device 420, or any storage device), and/or a route directing to a specific location. The guide information may include a video, an audio, a picture, or the like, or a combination thereof. FIGS. 8 through 11 illustrate exemplary guide pictures according to some embodiments of the present disclosure. As illustrated in FIG. 8, a patient may be guided to have the two arms naturally lower down and two palms face forward. As illustrated in FIG. 9, a patient may be guided to place the two hands behind his head and expose his chest. As illustrated in FIG. 10, a patient may be guided to place her hands on her abdomen and breathe in. As illustrated in FIG. 11, a patient may be guided to place her hands on her abdomen and breathe out. In some embodiments, the guide information may be presented via the output device 440 as a video clip demonstrating one or more actions with audio instructions.

In 504, the output device 440 may present the guide information. The output device 440 may present the guide information according to the play information in the at least one guide instruction. As illustrated elsewhere in the present disclosure, the play information may include a play mode, a play interval, a starting point, the pre-set number of playbacks, or the like, or a combination thereof. The play mode may include a loop playback, an order playback, an interval playback, etc.

In some embodiments, the output device 440 may present the guide information with one or more play intervals. For example, when the guide information includes two video clips, the output device 440 may present the two videos with a play interval (i.e., a time interval inbetween). The play interval may be determined according to the play information, for example, zero second, ten seconds, one minute, five minutes, or any other time period. As another example, when the guide information includes three video clips, the output device 440 may present the three videos with two play intervals inbetween, referred to as a first play interval and a second play interval. The first play interval and the second play interval may be determined according to the play information. The first play interval and the second play interval may be the same or different.

In some embodiments, the output device 440 may present the guide information according to the starting point to play the guide information. The starting point may be determined as a specific time point, e.g., 9:00 a.m. When the time reaches 9:00 a.m., the output device 440 may start to present the guide information. Further, the starting point may be determined according to a time point at which the scanning device 410 begins to scan a patient. For example, the starting point may be determined as the same as the beginning of the scanning of the scanning device 410, thus the output device 440 may start presenting the guide information simultaneously with the beginning of the scan. As another example, the starting point may be determined at a time point earlier than the beginning of the scanning of the scanning device 410, thus the output device 440 may start presenting the guide information at the time point before the scanning of the scanning device 410. As still another example, the starting point may be determined at a time point later than the beginning of the scanning of the scanning device 410, thus the output device 440 may start presenting the guide information at the time point later than the beginning of the scanning device 410 or during the scanning of the scanning device 410.

In 505, the scanning device 410 may scan a subject accompanied by the presentation of the guide information according to the one or more scan protocol. The scanning device 410 may scan the subject at a time point earlier than, later than, or at the same as the starting of presentation of the guide information. For example, when the scanning device 410 starts scanning and at the same time point the output device 440 starts to present the guide information, a patient may perform one or more specific actions according to the guide information. The one or more specific actions may satisfy a requirement of the scanning, for example, exposing the chest of the patient for scanning. Thus, during a scanning procedure, the patient may perform the one or more specific actions in accordance with the pre-recorded guide information, and the operator of the scanning device 410 may not need to verbally input the instructions.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 6:
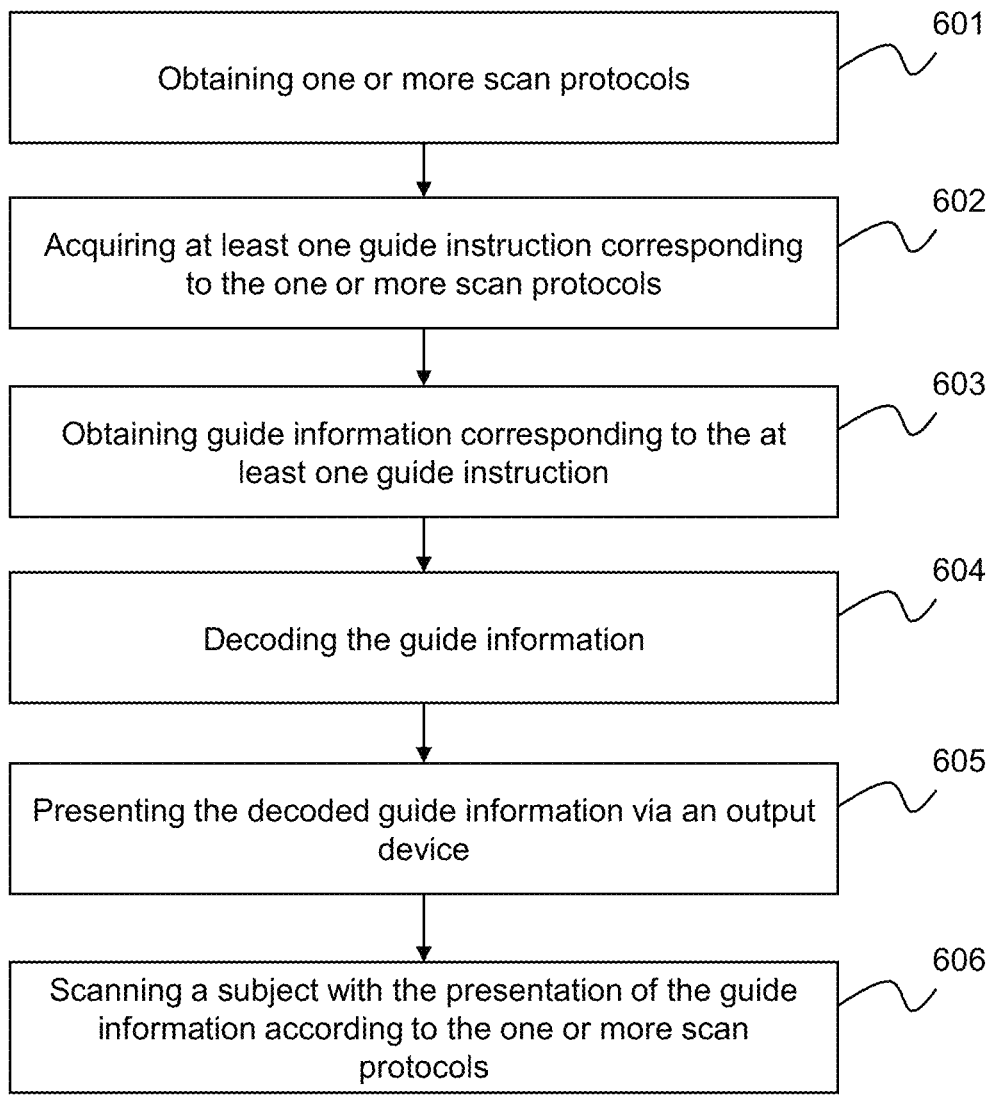
FIG. 6 is a flowchart illustrating another exemplary process for scanning a subject according to some embodiments of the present disclosure.

FIG. 6 is a flowchart illustrating another exemplary process for scanning a subject according to some embodiments of the present disclosure. Process 600 may be performed by processing logic that comprises hardware (e.g., circuitry, dedicated logic, programmable logic, microcode, etc.), software (e.g., instructions run on a processing device to perform hardware simulation), or a combination thereof. In some embodiments, process 600 may be performed by or be implemented on the medical device 110 and/or the processing device 140 of the medical system 100. The CPU 220 of the processing device 140 may execute the set of instructions and may accordingly perform the steps in the flowchart 600.

In 601, the control device 420 may obtain one or more scan protocols. The control device 420 may obtain the one or more scan protocols by performing one or more functions as illustrated in connection with operation 501. Further, the control device 420 may send the one or more scan protocols to the scanning device 410.

In 602, the control device 420 may obtain at least one guide instruction corresponding to the one or more scan protocols. The at least one guide instruction may include information relating to guide information, for example, the guide information itself, and/or a storage location of the guide information. Further, the at least guide instruction may include play information, device information, etc. In some embodiments, the control device 420 may obtain the at least one guide instruction by performing one or more functions as illustrated in connection with operation 502. Further, the control device 420 may send the at least one guide instruction to the decoding device 430.

In 603, the decoding device 430 may obtain guide information corresponding to the at least one guide instruction. In some embodiments, the decoding device 430 may obtain the guide information by performing one or more functions as illustrated in connection with operation 503.

In 604, the decoding device 430 may decode the guide information. The techniques used to decode the guide information may include Double Tone Multi Frequency (DTMF), Fast Fourier Transform (FFT), Discrete Fourier Transform (DFT), etc.

Further, the decoding device 430 may send the decoded guide information to be presented, i.e., the decoding device 430 may send the decoded guide information to the output device 440. In some embodiments, the decoding device 430 may send the decoded guide information to the output device 440 according to the device information and the play information. In some other embodiments, the decoding device 430 may send the decoded guide information to the output device 440 corresponding to the device information. In some other embodiments, the decoding device 430 may send the decoded guide information to the output device 440 in a condition defined by the play information. For example, if the play information defines that the play interval is five minutes, the decoding device 430 may send the decoded guide information to the output device 440 every five minutes. As another example, if the play information defines that the pre-set number of playbacks is three, the decoding device 430 may send the decoded guide information to the output device 440 three times. Accordingly, the output device 440 may present the decoded guide information without referring to the play information. Further, in some embodiments, the decoding device 430 may send the decoded guide information and the play information at the same time. The decoding device 430 may send the decoded guide information and the play information to the output device 440 according to the device information. In some other embodiments, the decoding device 430 may send the decoded guide information and play information to the output device 440 corresponding to the device information. In some other embodiments, the output device 440 may present the decoded guide information according to the play information. For example, if the play information defines that the play interval is five minutes, the output device 440 may present the decoded guide information every five minutes. As another example, if the play information defines that the pre-set number of playbacks is three, the output device 440 may present the decoded guide information three times.

In 605, the output device 440 may present the decoded guide information. In some embodiments, the output device 440 may present the decoded guide information by performing one or more functions as illustrated in connection with operation 504.

In 606, the scanning device 410 may scan a subject with the presentation of the guide information according to the one or more scan protocol. The scanning device 410 may scan the subject at a time point earlier than, later than, or at the same as the starting of presentation of the guide information.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, the order in which the operations of the process as illustrated in FIG. 6 and their respective description is merely an example and is not intended to be limiting. For example, the control device 420 may send the one or more scan protocols to the scanning device 410 and send the at least one guide instruction to the decoding device 430 simultaneously. As another example, the control device 420 may send the one or more scan protocols at the same time as the decoding device 430 sending the decoded guide information. As still another example, the control device 420 may send the one or more scan protocols after the output device 440 presenting the decoded guide information.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system for medical imaging, comprising:
at least one storage medium including a set of instructions for medical imaging; and
at least one processor in communication with the storage medium, wherein when executing the set of instructions, the at least one processor is directed to:
obtain one or more scan protocols;
acquire at least one guide instruction corresponding to the one or more scan protocols according to at least one predetermined relationship between the at least one guide instruction and the one or more scan protocols, wherein the at least one guide instruction includes device information and play information, and wherein the play information includes at least one of a play mode, a play interval, or a pre-set number of playback;
obtain guide information corresponding to the at least one guide instruction;
identify an output device according to the device information;
present the guide information, via the output device, according to the play information; and
scan a subject with the presentation of the guide information according to the one or more scan protocols.

2. The system of claim 1, wherein the at least one processor is further configured to decode the guide information and send the decoded guide information to the output device.

3. The system of claim 2, wherein the at least one processor is further configured to extract the guide information from the at least one guide instruction.

4. The system of claim 2, wherein the at least one processor is further configured to acquire a storage location of the guide information and retrieve the guide information from the storage location.

5. The system of claim 2, wherein the at least one processor is further configured to send the decoded guide information to the output device according to the device information and the play information.

6. The system of claim 2, wherein the at least one processor is further configured to send the decoded guide information and the play information to the output device according to the device information, and the output device is further configured to present the decoded guide information according to the play information.

7. The system of claim 6, wherein the play information includes the play interval.

8. The system of claim 1, wherein the guide information includes at least one of a picture, an audio, or a video.

9. The system of claim 1, wherein the presentation of the guide information is synchronous to the scanning of the subject according to the one or more scan protocols.

10. The system of claim 1, wherein the output device includes at least one of a display, a projector, or a head-mounted virtual reality device.

11. A method implemented on a system, the system including at least one processor and a storage device, the method comprising:
obtaining one or more scan protocols;
acquiring at least one guide instruction corresponding to the one or more scan protocols according to at least one predetermined relationship between the at least one guide instruction and the one or more scan protocols, wherein the at least one guide instruction includes device information and play information, and wherein the play information includes at least one of a play mode, a play interval, or a pre-set number of playback;
obtaining guide information corresponding to the at least one guide instruction;
identify an output device according to the device information;
presenting the guide information via an output device according to the play information; and
scanning a subject with the presentation of the guide information according to the one or more scan protocols.

12. The method of claim 11, further comprising:
decoding the guide information; and
sending the decoded guide information to the output device.

13. The method of claim 11, wherein obtaining guide information corresponding to the at least one guide instruction includes:
extracting the guide information from the at least one guide instruction.

14. The method of claim 11, wherein obtaining guide information corresponding to the at least one guide instruction includes:
acquiring a storage location of the guide information; and retrieving the guide information from the storage location.

15. The method of claim 12, wherein
sending the decoded guide information to the output device includes sending the decoded guide information to the output device according to the device information and the play information.

16. The method of claim 12, wherein
sending the decoded guide information to the output device includes sending the decoded guide information and the play information to the output device according to the device information, and
presenting the guide information via the output device includes presenting the decoded guide information according to the play information.

17. The method of claim 16, wherein the play information includes the play interval.

18. The method of claim 12, wherein the guide information includes at least one of a picture, an audio, or a video.

19. The method of claim 11, wherein the presentation of the guide information is synchronous to the scanning of the subject according to the one or more scan protocols.

20. A non-transitory computer readable medium embodying a computer program product, the computer program product comprising instructions configured to cause a computing system to:
obtain one or more scan protocols;
acquire at least one guide instruction corresponding to the one or more scan protocols according to at least one predetermined relationship between the at least one guide instruction and the one or more scan protocols, wherein the at least one guide instruction includes device information and play information, and wherein the play information includes at least one of a play mode, a play interval, or a pre-set number of playback;
obtain guide information corresponding to the at least one guide instruction;
identify an output device according to the device information;
present the guide information via an output device according to the play information; and
scan a subject with the presentation of the guide information according to the one or more scan protocols.

* * * * *